(12) United States Patent
Wei et al.

(10) Patent No.: US 8,158,409 B2
(45) Date of Patent: Apr. 17, 2012

(54) NANOSCALE SURFACE PLASMONICS SENSOR WITH NANOFLUIDIC CONTROL

(75) Inventors: Jianjun Wei, Madison, AL (US); Sameer Singhal, Huntsville, AL (US); David Hennessey Waldeck, Pittsburgh, PA (US); Matthew Joseph Kofke, Pittsburgh, PA (US)

(73) Assignees: CFD Research Corporation, Huntsville, AL (US); University of Pittsburgh, Pittsburgh, PA (US)

( * ) Notice: Subject to any disclaimer, the term of this patent is extended or adjusted under 35 U.S.C. 154(b) by 293 days.

(21) Appl. No.: 12/685,487

(22) Filed: Jan. 11, 2010

(65) Prior Publication Data

US 2011/0168559 A1    Jul. 14, 2011

(51) Int. Cl.
*C12M 1/34* (2006.01)

(52) U.S. Cl. ....... 435/287.1; 385/12; 385/129; 385/130; 422/82.11; 435/287.2; 435/288.4; 435/288.7; 435/808; 436/164; 436/524; 436/525; 436/805

(58) Field of Classification Search ........................ None
See application file for complete search history.

(56) References Cited

U.S. PATENT DOCUMENTS

| | | | |
|---|---|---|---|
| 7,169,251 B2 * | 1/2007 | Guo et al. | 156/292 |
| 7,399,445 B2 * | 7/2008 | Kuroda et al. | 422/504 |
| 7,426,040 B2 | 9/2008 | Kim | |
| 2003/0132392 A1 * | 7/2003 | Kuroda et al. | 250/397 |
| 2004/0197843 A1 * | 10/2004 | Chou et al. | 435/7.92 |
| 2009/0181857 A1 * | 7/2009 | Wei et al. | 506/9 |

FOREIGN PATENT DOCUMENTS

| WO | WO 2008111745 A1 | 9/2008 |
|---|---|---|
| WO | WO 2008136734 A1 | 11/2008 |

OTHER PUBLICATIONS

Jung et al, "High-sensitivity surface plasmon resonance spectroscopy based on a metal nanoslit array", Applied Physics Letters, (2006), 88, 243105.*
Lee et al, "Sensitive detection of nanoparticles using metallic nanoslit arrays", Applied Physics Letters, (2007), 90, 233119.*
Cheng, Gary J. et al. (2005) "Design and fabrication of a hybrid nanofluidic channel" J. Nicro/Nanolithography, 04 (01):013009.
Choi, Soobong et al. (2008) "Spatio-Spectral Measurement of a Surface Plasmon Polariton in a Gold Nano-Slit Array" J. Korean Physical Society, 53(2): 713-716.
Lee, K-L et al. (2007) "Tailor-made nanoslit structure which offers higher RIU sensitivity due to the extraordinary transmission of transverse magnetic wave in the nano slit gap" Proceedings of the SPIE 6641, 66411N.
Lee, K.L. et al.(2007) "Nanoslits have been successfuly fabricated and used to demonstrate on transmission SPR sensor applications" Appl. Phys. Lett.90:233119.
Ieebeeck, A. et al. (2007) "An integrated microfluidics based nanohol array chip device was developed for biomolecule adsorption detection in transmission SPR" Anal Chem. 79:4094-4100.
Ferreira, J. et al. (2009) "Attomolar Protein Detection Using in-Hole Surface Plasmon Resonance" J. Am. Chem. Soc., Article ASAP • DOI: 10.1021/ja807704v Downloaded from http://pubs.acs.org on Jan. 7, 2009.

* cited by examiner

*Primary Examiner* — Chris L Chin
(74) *Attorney, Agent, or Firm* — Maschoff Gilmore & Israelsen

(57) ABSTRACT

A microfluidically-controlled transmission mode nanoscal surface plasmonics sensor device comprises one or more arrays of aligned nanochannels in fluid communication with inflowing and outflowing fluid handling manifolds that control the flow of fluid through the array(s). Fluid comprising a sample for analysis is moved from an inlet manifold, through the nanochannel array, and out through an exit manifold. The fluid may also contain a reagent used to modify the interior surfaces of the nanochannels, and/or a reagent required for the detection of an analyte.

21 Claims, 5 Drawing Sheets

NANOSCALE SURFACE PLASMONICS SENSOR WITH NANOFLUIDIC CONTROL

STATEMENT REGARDING FEDERALLY SPONSORED RESEARCH OR DEVELOPMENT

The Federal Government has certain rights pertaining to the present invention pursuant to Contract No.: NNX-08-CD-36 awarded by the National Aeronautics and Space Administration.

CROSS-REFERENCE TO RELATED APPLICATIONS

Not Applicable

BACKGROUND OF THE INVENTION

1. Field of the Invention

The invention relates to a nanoscale surface plasmonics sensor comprising a fluid control system for delivering fluids to the sensor, and a quantitative protein assay method.

2. Description of Related Art

Conventional quantitative protein assays of bodily fluids typically involve multiple steps to obtain desired measurements. Such methods are not well suited for fast and accurate assay measurements in austere environments such as spaceflight and in the aftermath of disasters. Consequently, there is a need for a protein assay technology capable of routinely monitoring proteins in austere environments. For example, there is an immediate need for a urine protein assay to assess astronaut renal health during spaceflight. The disclosed nanoscale surface plasmonics sensor provides a core detection method that can be integrated to a lab-on-chip device that satisfies the unmet need for such a protein assay technology.

Assays based upon combinations of nanoholes, nanorings, and nanoslits with transmission surface plasmon resonance (SPR) are used for assays requiring extreme sensitivity and are capable of detecting specific analytes at concentrations as low as $10^{-14}$ M in well controlled environments. Existing SPR-based sensors, however, do not lend themselves to repetitive assays of biological fluids because they are not compatible with fluidic control systems, sample handling, and washing between samples.

The present SPR sensor with nanofluidic control overcomes the aforementioned limitations associated with existing protein assays. The SPR-based sensor provides for a protein sensor and assay method that may also be used for the detection and quantitation of a wide variety of analytes from a wide variety of sources.

BRIEF SUMMARY OF THE INVENTION

The present invention incorporates transmission mode nanoplasmonics and nanofluidics into a single, microfluidically-controlled device. The device comprises one or more arrays of aligned nanochannels that are in fluid communication with inflowing and outflowing fluid handling manifolds that control the flow of fluid through the array(s). The array acts as an aperture in a plasmonic sensor. Fluid, in the form of a liquid or a gas and comprising a sample for analysis is moved from an inlet manifold, through the nanochannel array, and out through an exit manifold. The fluid may also contain a reagent used to modify the interior surfaces of the nanochannels, and/or a reagent required for the detection of an analyte.

The device operates in a transmission mode configuration in which light is directed at one planar surface of the array, which functions as an optical aperture. The incident light induces surface plasmon light transmission from the opposite surface of the array. The presence of a target analyte is detected by changes in the spectrum of light transmitted by the array when a target analyte induces a change in the refractive index of the fluid within the nanochannels.

This occurs, for example, when a target analyte binds to a receptor fixed to the walls of the nanochannels in the array. Independent fluid handling capability for individual nanoarrays on a nanofluidic chip containing a plurality of nanochannel arrays allows each array to be used to sense a different target analyte and/or for paired arrays to simultaneously analyze control and test samples in parallel.

DETAILED DESCRIPTION OF THE INVENTION

Nanofluidics, as used herein, refers to the behavior, manipulation, and control of fluids that are confined inside flow channel structures in which the cross-sectional dimensions are between 10 and 800 nanometers.

A "nanochannel," as used herein, is a tubular structure having a rectangular cross-sectional shape. The dimensions of a channel are described by length, depth, and width, wherein the depth is measured perpendicular to the plane of a nanofluidic chip containing the nanochannel and length and width are measured in directions lying in the plane of a wafer containing a nanochannel array. Maximum depth and width, when used to describe a nanochannel having a rectangular cross-section, refer to a channel having a constant width and depth.

Figure 1:
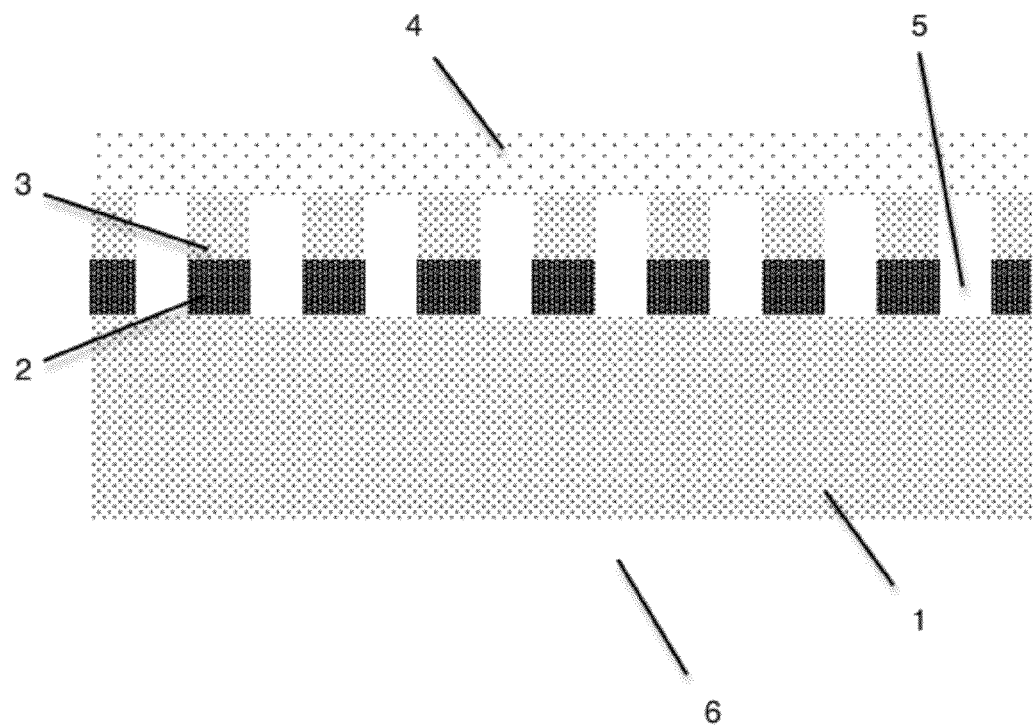
FIG. 1 is an end-on cross section drawing showing the construction of a nanochannel array according to the present invention.

The sensor comprises a flat, transparent dielectric substrate 1 upon which a 30 nm to 500 nm thickness metal film 2 is formed (FIG. 1). The metal film 2 may be formed directly on the substrate 1 or the substrate 1 may be coated with a 1-10 nm layer of another metal such as chromium or titanium to promote adhesion of the metal layer 2 to the substrate 1. The metal film 2, in turn, is covered with a 1-50 nm thickness of a transparent dielectric layer 3. Aligned, uniform nanoslits having a width of between 10 nm and 800 nm, preferably 30 nm to 300 nm, are milled all the way through the transparent dielectric layer 3 and the metal film 2 with a regular periodicity ranging from 100 nm to 800 nm to form a nanoslit array. The nanoslits may be milled, for example, by means of a dual beam scanning electron microscope/focused ion beam. A transparent top layer 4 covers the transparent dielectric layer and seals the tops of the nanoslits to form nanochannels 5 which, in turn, form a nanochannel array 6. The number of nanochannels per array may range from 5 to 5000 and preferably from 20 to 100. The metal film 2 may be made of any suitable metal and preferably a metal selected from Au, Ag, Cu, Pt, or combinations thereof. The transparent dielectric substrate 1, dielectric layer 3, and transparent layer 4 may be made, for example of PDMS, PMMA, quartz, SiOx, or a glass. In preferred embodiments, the substrate is made of quartz or a glass, the metal layer is made of gold or silver, the dielectric layer is made from SiOx or a glass, and the transparent top layer is made of PDMS or PMMA.

EXAMPLE

Array Fabrication

A quartz microscope slide is cleaned with a piranha solution (3:1$H_2SO_4$/$H_2O_2$) at 80° C. for at least 10 minutes, rinsed with deionized water, and dried under nitrogen. A 1-3 nm Ti layer is deposited on the quartz surface using an e-beam evaporator. A 100 nm-200 nm Au film is deposited on the Ti layer. Nanoslits are milled with a focused ion beam system. For a typical nanoslit array, sets of 40 individual nanoslits are fabricated with a spacing defined by the array's periodicity. For transmission measurements, a reference window is milled into the same Au film that contains the nanoslit arrays. Normal beam conditions for the reference window are 30 kV and 30 pA.

Figure 2:
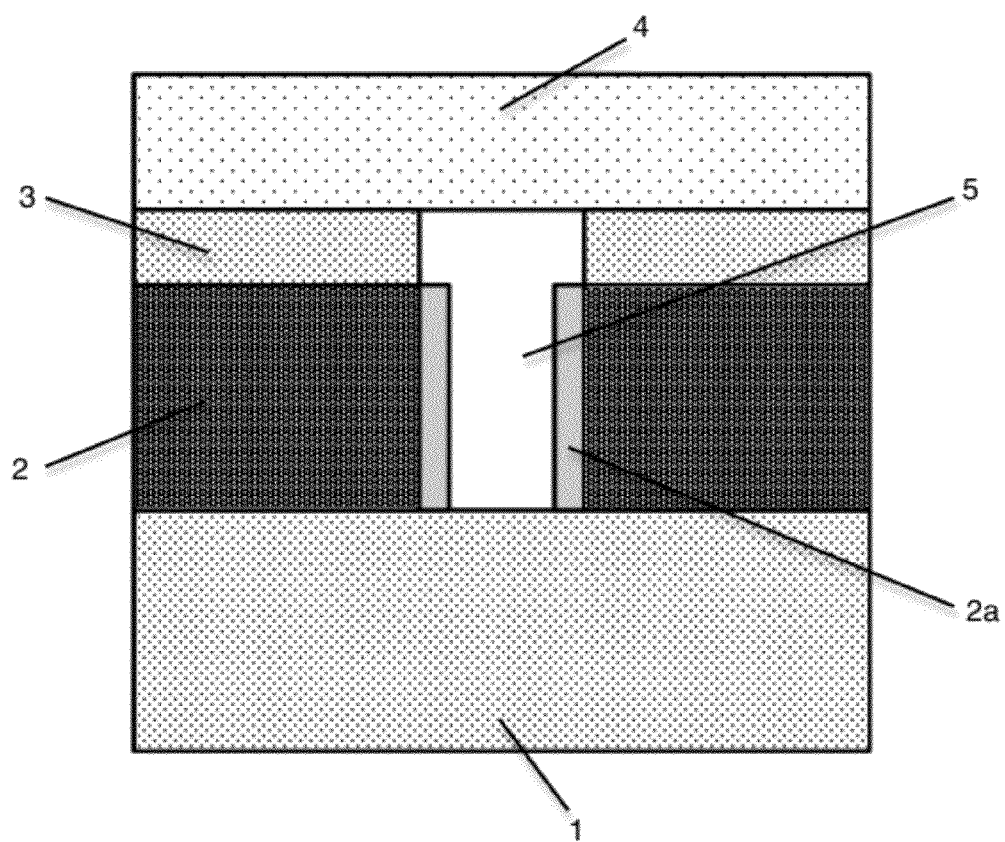
FIG. 2 is an end-on cross-section of a nanochannel coated on its metal surface with an analyte-binding material.

All or a portion of the luminal surfaces of the nanochannels in an array may be modified to control their binding and or light transmission characteristics such as nonspecific binding and refractive index. To facilitate selective detection of particular target analytes, all or a portion of the lumenal surfaces of the nanochannels may be coated with substances that selectively bind to one or more analytes. For example, a self-assembling monolayer 2a of molecules capable of cross-linking or associating with target analyte specific binding agents may be formed on the lumenal surfaces of the metal layers 2 of the nanochannels 5 (FIG. 2). To selectively detect serum albumin, for example, in urine or other sample fluids, gold surfaces in nanochannels may be coated with a monolayer of N-succinimidyl-3-(2-pyridyldithio)propionate (SPDP) with a cross-linking group for anti-albumin antibody immobilized to the nanoslit surface, followed by coupling of the SPDP with anti-albumin antibody. To selectively detect IgG, protein A may be immobilized to gold nanoslit surfaces via SPDP.

Figure 3:
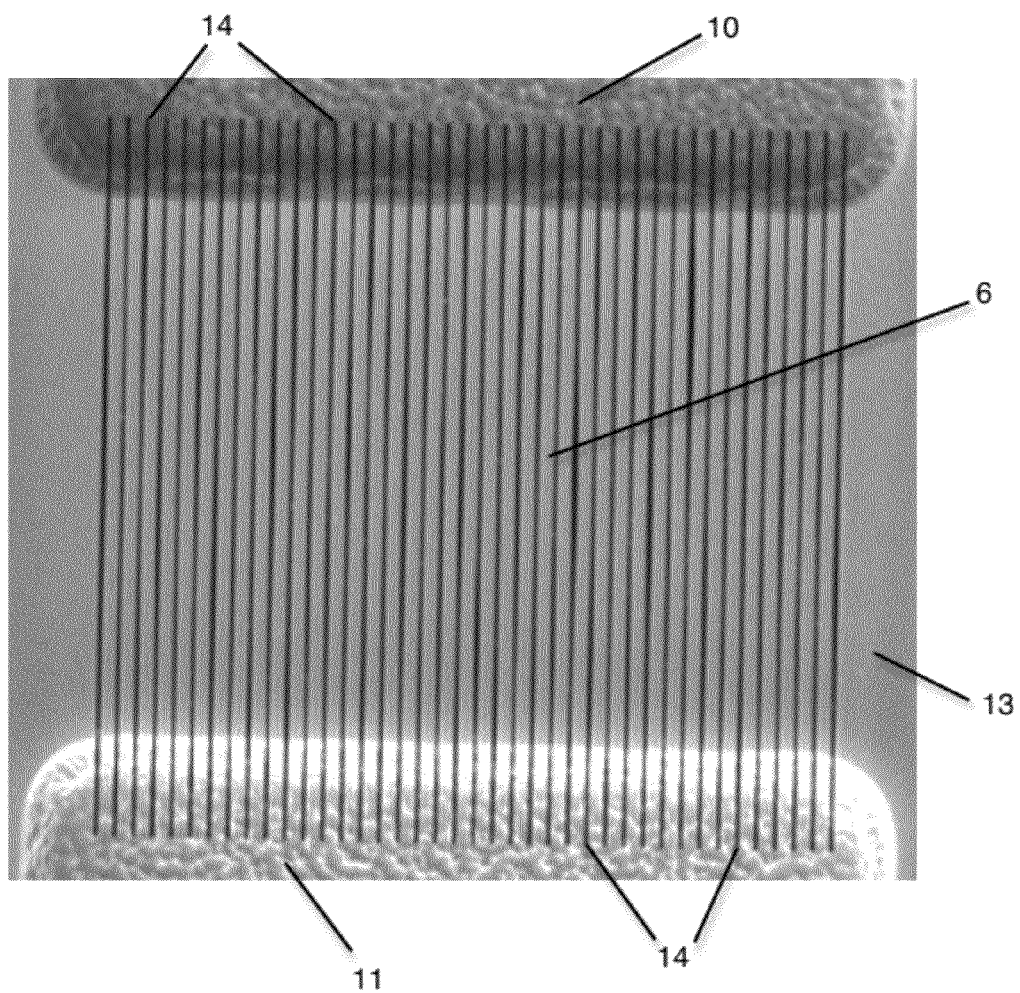
FIG. 3 is an illustration of a nanochannel array with microfluidic fluid control.
Figure 4:
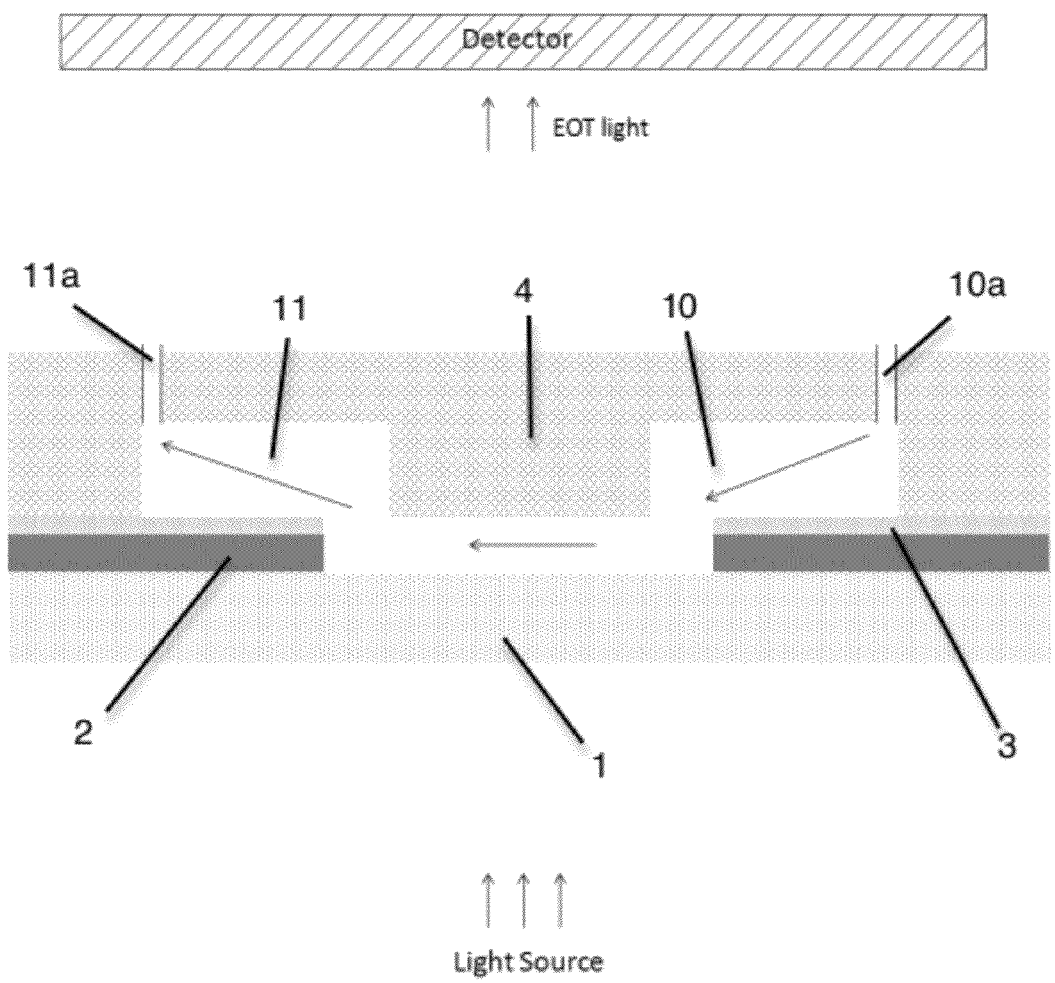
FIG. 4 is a side cross-section view along a nanochannel of a nanofluidic wafer.

To move fluids, including samples and reagents through the nanochannels in an array, the nanochannels are in fluid communication with inlet and outlet manifolds and means for moving fluid. The nanochannels may be formed in such a way as to have open ends that communicate directly with manifolds that overlap the nanochannels in the wafer containing the array. Such an arrangement can be formed, for example, by etching inlet and outlet manifolds into the substrate, metal, and dielectric layers before applying the transparent top layer of the wafer. Alternatively, the nanochannels may be formed as sealed tubes and communicate with manifolds located in a plane above or below the plane of the nanochannel array. FIG. 3 is a scanning electron microscope (SEM) image of a wafer 13 comprising 3 μm deep inlet 10 and outlet 11 manifolds formed in a transparent top layer overlapping the sealed ends 14 of 125 nm deep nanochannels in a nanochannel array 6. FIG. 4 is a side cross-section view (not to scale) showing the relative positions of the wafer components including nanochannel inlet 10a and outlet 11a as well as the relative positions of a light source and detector in a sensor device comprising the wafer. Arrows within the wafer indicate the path of fluid flow, while arrows outside the wafer indicate the direction of light directed toward and light transmitted from the wafer.

Figure 5:
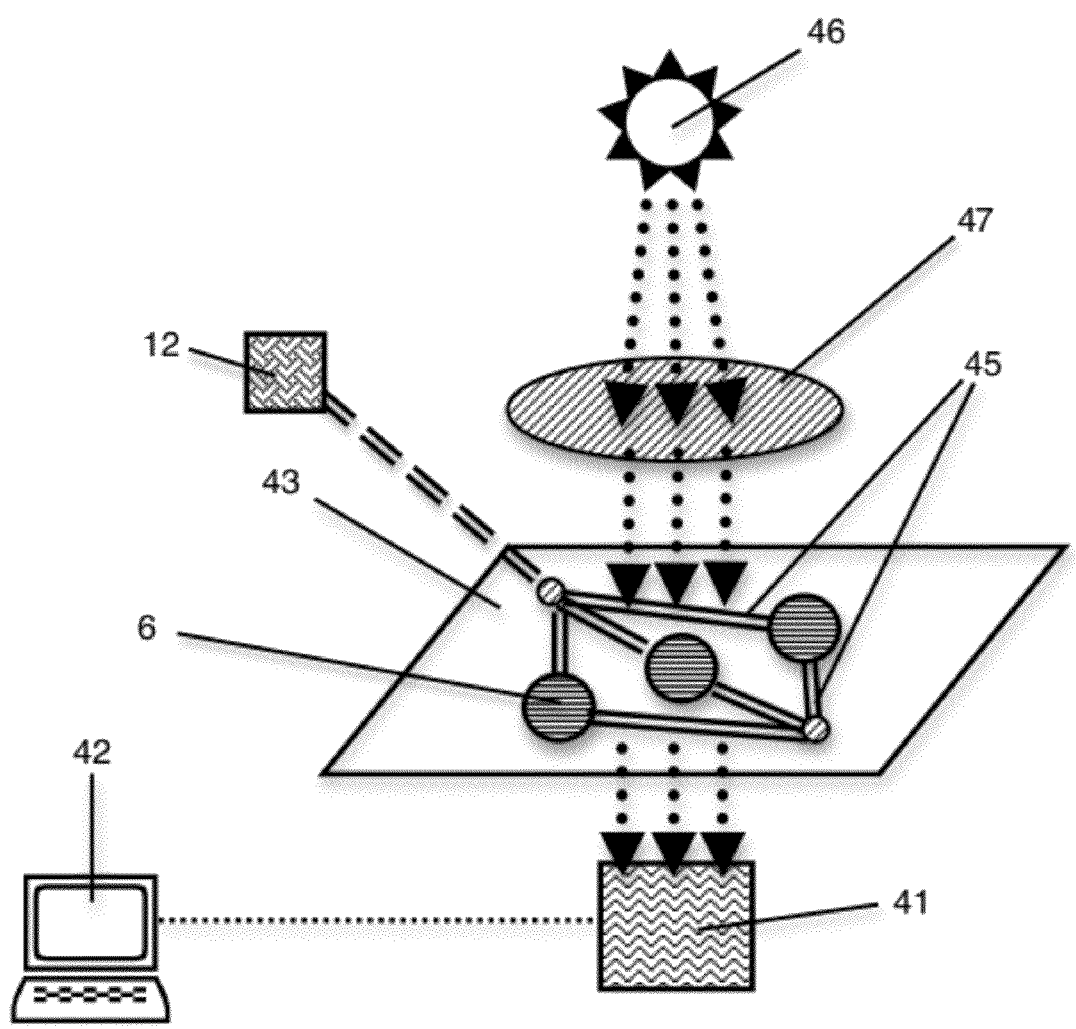
FIG. 5 illustrates a urine protein analysis device comprising three nanochannel plasmonic sensor arrays.

A protein SPR sensor device comprising three nanochannel arrays 6 is illustrated in FIG. 5. The apparatus consists of a light source 46, an optical detection system 41, a data acquisition unit 42, and a microfluidic-based urine protein assay cartridge 43 comprising three nanochannel plasmonic sensor arrays 6. The surfaces of the nanochannels in the plasmonic sensor arrays 6 are functionalized with an ultrathin film of receptors that may be nonspecific for binding to protein generally or may specific for binding target proteins to be detected in the urine. The sensor integrates to a microfluidic network 45 and pumping means 12 configured for reagent and fluid flow handling. Nanoslit array transmission spectra of light from a white light source 46 incident upon the top of the arrays 6 are captured by an optical detection system 41 comprising a fiber optical array, mini-spectrometer or CCD, for example, and processed and stored in a data acquisition unit 42.

Fluid communication between a nanochannel array 6 and fluid handling manifolds allows fluid to be moved through the nanochannel array 6 using a pumping means 12 configured to move fluid through the nanochannel array 6. The pumping means 12 includes, for example, electrokinetic, electrothermal, and peristaltic pumps and may be incorporated into the cartridge 43 or may be a separate unit as shown in FIG. 5. The fluid handling capability of an individual nanoarray may be incorporated into nanofluidic chips containing a plurality of nanochannel arrays with each array being used to sense a different target analyte, for example, or to assay test and control samples simultaneously.

Devices of this type may also be used to detect a wide variety of analytes including proteins in biological samples such as urine, blood, saliva, as well as samples of non-biological origin.

Reference to particular embodiments of the present invention have been made for the purpose of describing a nanoscale surface plasmonics sensor with nanofluidic control. It is not intended that such references be construed as limitations upon the scope of this invention except as set forth in the following claims.

The invention claimed is:

1. A nanofluidic device comprising a planar wafer, said wafer comprising:
   a planar transparent dielectric substrate having a top surface and a bottom surface;
   a metal layer having a thickness of between 30 and 500 nm formed on the top surface of the substrate;
   a transparent dielectric layer having a thickness of between 1 nm and 50 nm formed on the metal layer;
   a plurality of parallel nanoslits cut into the metal and transparent dielectric layers in the plane of the substrate to form a nanoslit array, said nanoslits having a width of between 10 nm and 800 nm and spaced between 100 nm and 800 nm apart, and completely penetrating the transparent dielectric and metal layers of the wafer; and
   a transparent top layer covering the nanoslit array to form a plurality of parallel nanochannels forming a square or rectangular nanochannel array with a surface area of between 1.0 μm$^2$ and 100 mm$^2$
   wherein:
   the transparent dielectric substrate forms a bottom lumenal surface of each nanochannel, the metal and transparent dielectric layers form side lumenal surfaces of each nanochannel, and the transparent top layer forms a top lumenal surface of each nanochannel; and
   each nanochannel comprises a fluid inlet and a fluid outlet.

2. The nanofluidic device of claim 1, wherein a plurality of the nanochannels are in fluid communication with a common fluid inlet manifold through their fluid inlets and a common fluid outlet manifold through their fluid outlets.

3. The nanofluidic device of claim 2, wherein said plurality of the nanochannels comprises all of the nanochannels in the array.

4. The nanofluidic device of claim 1, and further comprising a light source configured to direct light onto a top or bottom surface, respectively, of the nanochannel array and a light detector configured to detect light emission from a bottom or top surface, respectively, of the nanochannel array.

5. The nanofluidic device of claim 1, wherein the nanochannels have a uniform width of from 10 nm to 800 nm.

6. The nanofluidic device of claim 1, wherein the nanochannels have a uniform width of from 30 nm to 300 nm.

7. The nanofluidic device of claim 1, and further comprising metal nanoparticles distributed on the bottom lumenal surfaces of the nanochannels, said metal nanoparticles having cross-sectional dimensions of from 1 nm-200 nm.

8. The nanofluidic device of claim 7, wherein the metal nanoparticles are gold nanoparticles and/or silver nanoparticles.

9. The nanofluidic device of claim 7, wherein the metal nanoparticles are distributed randomly or in an ordered pattern.

10. The nanofluidic device of claim 1, wherein one or more lumenal surfaces of the nanochannels in the array is coated by a self-assembled monolayer or polymer film.

11. The nanofluidic device of claim 1, wherein the metal layer is formed directly on the substrate.

12. The nanofluidic device of claim 1, wherein the metal layer is formed on a primer metal coating that promotes the adhesion of the metal layer to the substrate.

13. A method for making a nanofluidic device comprising the steps of:
a) forming a metal film on a transparent dielectric substrate;
b) forming a dielectric layer on said metal film;
c) milling through the dielectric layer and metal film to form an array of nanoslits; and either
d) forming or applying a transparent top layer covering the array of nanoslits, thereby sealing the nanoslits to form an array of nanochannels, wherein each nanochannel comprises an inlet and an outlet located at opposite ends of the channel or
e) forming or applying a transparent layer covering the array of nanoslits, thereby sealing the nanoslits to form an array of closed nanochannels and forming an inlet and an outlet at opposite ends of each nanochannel to form an array of nanochannels
wherein:
the transparent top layer is a polymer, glass, or quartz and
the transparent dielectric substrate forms a bottom lumenal surface of each nanochannel, the metal and transparent dielectric layers form side lumenal surfaces of each nanochannel, and the transparent top layer forms a top lumenal surface of each nanochannel.

14. The method of claim 13, and further comprising the step of forming or distributing nanoparticles on the bottom lumenal surfaces of the nanochannels.

15. The method of claim 13, and further comprising the step of placing the nanochannels in fluid communication with a fluid moving means configured to flow a fluid through the nanochannels.

16. The method of claim 13 and further comprising the step of coating a lumenal surface of the nanochannels with a self-assembled monolayer or polymer film.

17. The method of claim 13, wherein the nanochannels have a uniform width of from 10 nm to 800 nm.

18. The method of claim 13, wherein the nanochannels have a uniform width of from 30 nm to 300 nm.

19. A quantitative protein assay apparatus comprising at least one surface plasmonics sensor, said apparatus comprising:
a) a nanofluidic device comprising a planar wafer, said wafer comprising:
a planar transparent dielectric substrate having a top surface and a bottom surface;
a metal layer having a thickness of between 10 and 500 nm formed on the top surface of the substrate;
a transparent dielectric layer having a thickness of between 50 nm and 100 nm formed on the metal layer;
a plurality of parallel nanoslits cut into the metal and transparent dielectric layers in the plane of the substrate to form a nanoslit array, said nanoslits having a width of between 10 nm and 800 nm and spaced between 100 nm and 800 nm apart, and completely penetrating the transparent dielectric and metal layers of the wafer; and
a transparent top layer covering the nanoslit array to form a plurality of parallel nanochannels forming a square or rectangular nanochannel array with a surface area of between 1.0 $\mu m^2$ and 100 $mm^2$
wherein:
the transparent dielectric substrate forms a bottom lumenal surface of each nanochannel, the metal and transparent dielectric layers form side lumenal surfaces of each nanochannel, and the transparent top layer forms a top lumenal surface of each nanochannel; and
each nanochannel comprises a fluid inlet and a fluid outlet;
b) a light source configured to direct light onto a top or bottom surface, respectively, of the nanochannel array:
c) a light detector configured to detect light emission from a bottom or top surface, respectively, of the nanochannel array; and
d) a computer in digital communication with the light source and the light detector.

20. The quantitative protein assay apparatus of claim 19, wherein a plurality of the nanochannels are in fluid communication with a common fluid inlet manifold through their fluid inlets and a common fluid outlet manifold through their fluid outlets.

21. The quantitative protein assay apparatus of claim 19, wherein a lumenal surface of the nanochannels in the array is modified by a self-assembled monolayer or polymer film.

* * * * *